(12) United States Patent
Higuchi et al.

(10) Patent No.: US 9,762,179 B2
(45) Date of Patent: Sep. 12, 2017

(54) SOLAR CELL TESTING APPARATUS AND SOLAR CELL TESTING METHOD

(71) Applicant: HIOKI DENKI KABUSHIKI KAISHA, Nagano (JP)

(72) Inventors: Masao Higuchi, Nagano (JP); Fumio Tokutake, Nagano (JP)

(73) Assignee: HIOKI DENKI KABUSHIKI KAISHA, Nagano (JP)

( * ) Notice: Subject to any disclaimer, the term of this patent is extended or adjusted under 35 U.S.C. 154(b) by 0 days.

(21) Appl. No.: 15/139,605

(22) Filed: Apr. 27, 2016

(65) Prior Publication Data

US 2016/0329863 A1 Nov. 10, 2016

(30) Foreign Application Priority Data

May 8, 2015 (JP) ................................. 2015-095351

(51) Int. Cl.
*G01R 31/26* (2014.01)
*H02S 50/10* (2014.01)
*H02S 50/00* (2014.01)

(52) U.S. Cl.
CPC .............. *H02S 50/10* (2014.12); *H02S 50/00* (2013.01)

(58) Field of Classification Search
CPC G01R 31/26; G01R 31/2642; G01R 31/2648; G01R 31/2831; G01R 31/31702; G01R 31/40; G01R 31/42; F21S 8/006; H01L 22/00; H01L 31/04; H01L 51/0031
See application file for complete search history.

(56) References Cited

U.S. PATENT DOCUMENTS

| | | | |
|---|---|---|---|
| 6,512,458 B1* | 1/2003 | Kobayashi | ............ H01L 31/044 |
| | | | 340/507 |
| 2011/0032099 A1 | 2/2011 | Giesler | |
| 2011/0079263 A1 | 4/2011 | Avrutsky | |
| 2015/0188487 A1 | 7/2015 | Yoshidomi et al. | |
| 2016/0294189 A1* | 10/2016 | Uno | ......................... G05F 1/67 |

FOREIGN PATENT DOCUMENTS

| | | |
|---|---|---|
| JP | 2011-66320 | 3/2011 |
| WO | 2014/007261 | 1/2014 |

OTHER PUBLICATIONS

Extended European Search Report, mailed Jul. 12, 2016 by the European Patent Office (EPO), for the related European Patent Application No. 16167898.2.

* cited by examiner

*Primary Examiner* — Tung X Nguyen
(74) *Attorney, Agent, or Firm* — Greenblum & Bernstein, P.L.C.

(57) ABSTRACT

A solar cell testing apparatus tests bypass diodes in a solar cell string, which is constructed of solar cell modules including solar cells and the bypass diodes, for open-position failures and includes: a unidirectional element connected between positive and negative electrodes of the solar cell string so as to permit passage of the current outputted when the solar cells generate power; a voltage applier that apples a test voltage, which exceeds a sum of forward direction voltages of the bypass diodes and sets the negative electrode potential higher than the positive electrode potential, across the positive and negative electrodes; a current detector that detects a current flowing in the solar cell string; and a processor that tests for open-position failures by comparing currents detected before and after application of the test voltage with the unidirectional ele- (Continued)

ment connected between the electrodes of the solar cell string.

4 Claims, 4 Drawing Sheets

SOLAR CELL TESTING APPARATUS AND SOLAR CELL TESTING METHOD

FIELD OF THE INVENTION

The present invention relates to a solar cell testing apparatus and a solar cell testing method that execute testing of bypass diodes used in solar cells.

DESCRIPTION OF THE RELATED ART

The solar cell testing apparatus (power conditioner) disclosed in Japanese Laid-open Patent Publication No. 2011-66320 is known as one example of this type of solar cell testing apparatus. This solar cell testing apparatus includes: a current sensor which is connected to a solar cell array, detects the current value of a current flowing in the solar cell array, and outputs a detection value; a voltage sensor that detects a voltage across both terminals of the solar cell array and outputs a detection value; an input capacitor; an MPPT (Maximum Power Point Tracking) control unit that carries out MPPT control based on the detection values of the current sensor and the voltage sensor to track a point where the output power of the solar cell array reaches a maximum; a DC-AC invertor that converts the DC current outputted from the solar cell array to AC and outputs the AC current to a load; an AC-DC convertor that converts an AC current from a commercial power source to a DC current; two switches for switching wiring when power is generated and when diagnosis is performed; a CPU that carries out control over a diagnosis process for the solar cell array and the bypass diodes in the solar cell array; and a memory that stores various information.

Here, the input capacitor functions as an input capacitor when power is generated, and during diagnosis, the discharging characteristics of the input capacitor are used to acquire the I-V characteristics of the solar cell array and the I-V characteristics of the bypass diodes. The current sensor and the voltage sensor have a function for detecting the current and voltage used during MPPT control, and are also used during diagnosis as sensors that detect current and voltage for acquiring the I-V characteristics of the solar cell array.

With this solar cell testing apparatus, during a diagnosis period that is set in advance in a time zone period where the solar power generation system does not generate power, the connection between the solar cell array and the solar cell testing apparatus (power conditioner) is cut by setting a first switch that was connected to wiring on the power generation side to a neutral position and switching a second switch that was connected to a DC-AC invertor side to the AC-DC convertor side. The AC current from the commercial power source is then converted by the AC-DC convertor to a DC current that charges the input capacitor. During charging, in order to acquire the I-V characteristics of the bypass diodes in particular, the input capacitor is charged so that it will discharge in the forward direction of the bypass diodes. After charging is complete, the second switch is set at a neutral position to cut off the input capacitor and the AC-DC convertor.

Next, a solar cell string that includes the bypass diodes to be tested is switched from wiring on the power generation side to wiring on the diagnosis side. After this the first switch is connected to the diagnosis wiring and the input capacitor that has been charged is discharged. The current value and voltage value during discharging are acquired from the current sensor and the voltage sensor and the I-V characteristics for the solar cell string to be tested are measured from the current value and the voltage value that have been acquired. Here, since the current when the input capacitor is discharged is a current that flows in the forward direction of the bypass diodes, the I-V characteristics when all of the bypass diodes included in the solar cell string are all normal differ to the I-V characteristics when any of the bypass diodes included in the solar cell string has failed in the open position.

With the solar cell testing apparatus described above, the I-V characteristics when all of the bypass diodes are normal are stored as one type of information in the memory, and by comparing the measured I-V characteristics with the normal I-V characteristics stored in the memory, it is possible to diagnose whether any of the bypass diodes has failed in the open position.

SUMMARY OF THE INVENTION

However, with the solar cell testing apparatus described above, there is the following problem to be solved. That is, the solar cell testing apparatus has a problem in that it is possible to carry out diagnosis only when the solar cells are not generating power or when the amount of generated power is extremely small).

To solve the problem described above, it is a principal object of the present invention to provide a solar cell testing apparatus capable of testing solar cells in a state where the solar cells are generating power.

To achieve the stated object, a solar cell testing apparatus according to the present invention tests bypass diodes in a solar cell string constructed by connecting a plurality of solar cell modules, which include solar cells and the bypass diodes, in series for failures in the open position; and the solar cell testing apparatus comprises a unidirectional element that is connected between a positive electrode and a negative electrode of the solar cell string with a polarity that permits passage of an output current outputted from the solar cell string when the solar cells generate power; a voltage applier capable of applying a test voltage, which has a voltage value that exceeds a sum of forward direction voltages of a plurality of bypass diodes and is a voltage such that a potential of the negative electrode is high relative to a potential of the positive electrode, across the positive electrode and the negative electrode of the solar cell string to which the unidirectional element is connected; a current detector that detects a current flowing in the solar cell string; and a processor that tests for failures in the open position by comparing the currents detected by the current detector before and after application of the test voltage in a state where the unidirectional element is connected between the positive electrode and the negative electrode of the solar cell string.

Also, the solar cell testing method to the present invention tests bypass diodes in a solar cell string constructed by connecting a plurality of solar cell modules, which include solar cells and the bypass diodes, in series for failures in the open position; and the solar cell testing method comprises applying, in a state where a unidirectional element is connected between a positive electrode and a negative electrode of the solar cell string with a polarity that permits passage of an output current outputted from the solar cell string when the solar cells generate power, a test voltage, that has a voltage value that exceeds a sum of forward direction voltages of a plurality of the bypass diodes and is a voltage such that a potential of the negative electrode is high relative to a potential of the positive electrode, across the positive electrode and the negative electrode of the solar cell string to which the unidirectional element is connected while detecting a current flowing in the solar cell string; and testing for failures in the open position by comparing the current before and after application of the test voltage in the state where the unidirectional element is connected between the positive electrode and the negative electrode.

With the solar cell testing apparatus and the solar cell testing method according to the present invention, the presence of open failures at bypass diodes is tested by comparing the currents detected by the current detecting unit before and after application of a test voltage, which has a voltage value that exceeds a sum of forward direction voltages of a plurality of bypass diodes and is a voltage such that a potential of the negative electrode is high relative to a potential of the positive electrode, between the positive electrode and the negative electrode of solar cell string that is being shorted by the unidirectional element.

Accordingly, with the solar cell testing apparatus and the solar cell testing method according to the present invention, even when the solar cell string is generating power and the open circuit voltage is extremely high, by shorting the solar cell string using the unidirectional element, it is possible for the test voltage for turning on the plurality of bypass diodes in the solar cell string to be a low voltage that is only slightly higher than the sum of the forward direction voltages of the bypass diodes (i.e., an extremely low voltage compared to the open-circuit voltage mentioned above). This means that it is possible to easily and reliably test the bypass diodes for failures in the open position, even when the solar cell string is generating power.

The solar cell testing apparatus according to the present invention, wherein the voltage applier includes a series circuit composed of a capacitor and a current limiting resistor; a power supply; and a switch that switches between a charging connection state where the series circuit is connected to the power supply and a discharging connection state where the series circuit is connected between the positive electrode and the negative electrode of the solar cell string, and when switching to the charging connection state, the switch is controlled to connect the power supply to the series circuit and the capacitor is charged using a DC voltage outputted from the power supply, and when switching to the discharging connection state, the switch is controlled to connect the series circuit between the positive electrode and the negative electrode of the solar cell string and a charging voltage of the capacitor that was charged in the charging connection state is applied between the positive electrode and the negative electrode as the test voltage.

With the solar cell testing apparatus according to the present invention, it is possible to easily construct the voltage applying unit of a series circuit composed of a capacitor and a current limiting resistor, a power supply (unipolar power supply), and a switch, without using an expensive power supply such as a bipolar power supply. This means that the solar cell testing apparatus can be manufactured at low cost.

The solar cell testing apparatus according to the present invention, wherein the processor executes control over the voltage applier to apply the charging voltage as the test voltage while gradually increasing the charging voltage until a upper limit voltage value set in advance is reached.

With the solar cell testing apparatus according to the present invention, since it is possible to gradually increase the test voltage applied from the voltage applying unit to the solar cell string, by stopping the application of the test voltage as soon as it has been detected that the bypass diodes are normal by comparing the currents before and after application of the test voltage detected by the current detecting unit, for example, it is possible to prevent failure of the bypass diodes due to the application of an excessive test voltage.

It should be noted that the disclosure of the present invention relates to the contents of Japanese Patent Application 2015-1595351 that was filed on May 8, 2015, the entire contents of which are herein incorporated by reference.

BRIEF DESCRIPTION OF THE DRAWINGS

These and other objects and features of the present invention will be explained in more detail below with reference to the attached drawings, wherein.

DESCRIPTION OF THE PREFERRED EMBODIMENTS

Figure 1:
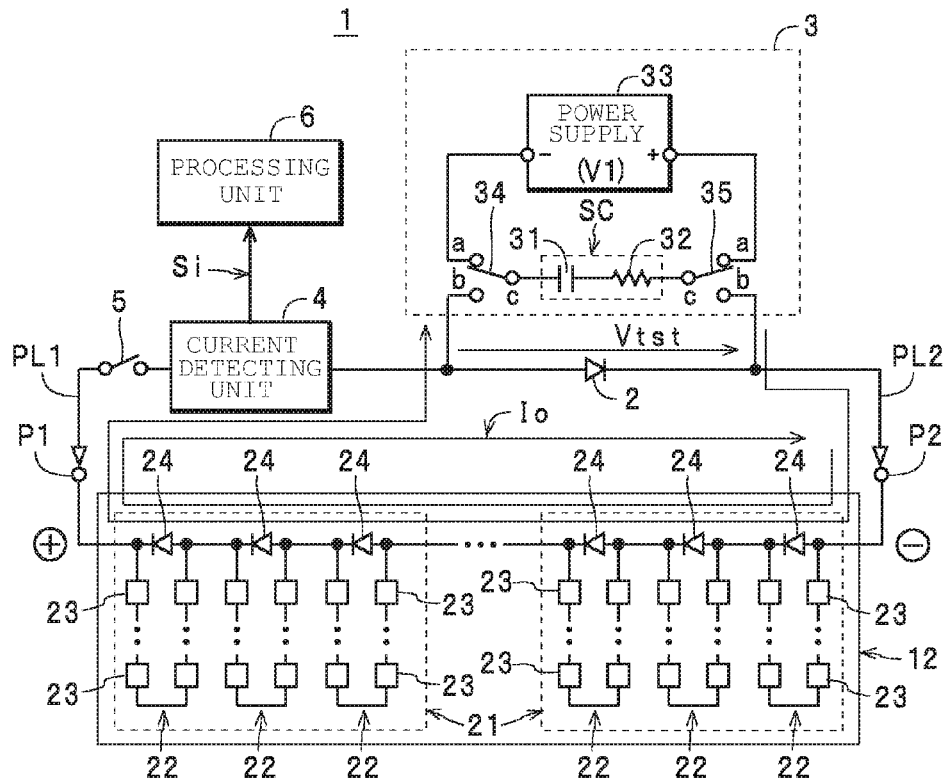
FIG. 1 depicts the configurations of a solar cell testing apparatus and a solar cell string.

Preferred embodiments of a solar cell testing apparatus and a solar cell testing method according to the present invention will now be described with reference to the attached drawings.

First, the configuration of a solar cell testing apparatus will be described with reference to the drawings.

First, the configuration of a solar cell testing apparatus 1 as the solar cell testing apparatus depicted in FIG. 1 will be described.

The solar cell testing apparatus 1 includes a unidirectional element (as examples, a diode or a transistor connected as a diode, in the present embodiment, a diode) 2, a voltage applying unit 3, a current detecting unit 4, a switch 5, and a processing unit 6, and tests whether bypass diodes 24 disposed in a solar cell string 12 to be tested, described later, have failed in the open position.

Here, an overview of a solar cell string 12 will be given before a detailed description of the respective component elements of the solar cell testing apparatus 1. As one example, the solar cell string 12 is a component unit of a solar cell array 11 like that depicted in FIG. 2 that is installed on a building such as an office block or a house, with a plurality of the solar cell strings 12 constructing one solar cell array 11. As one example, a plurality of solar cell strings 12 are connected in parallel via blocking diodes 14 in a junction box 13. Using switches 15 disposed inside the junction box 13, it is possible to cut off the respective solar cell strings 12 from other solar cell strings 12 or restore the solar cell strings 12 to a parallel-connected state.

Figure 2:
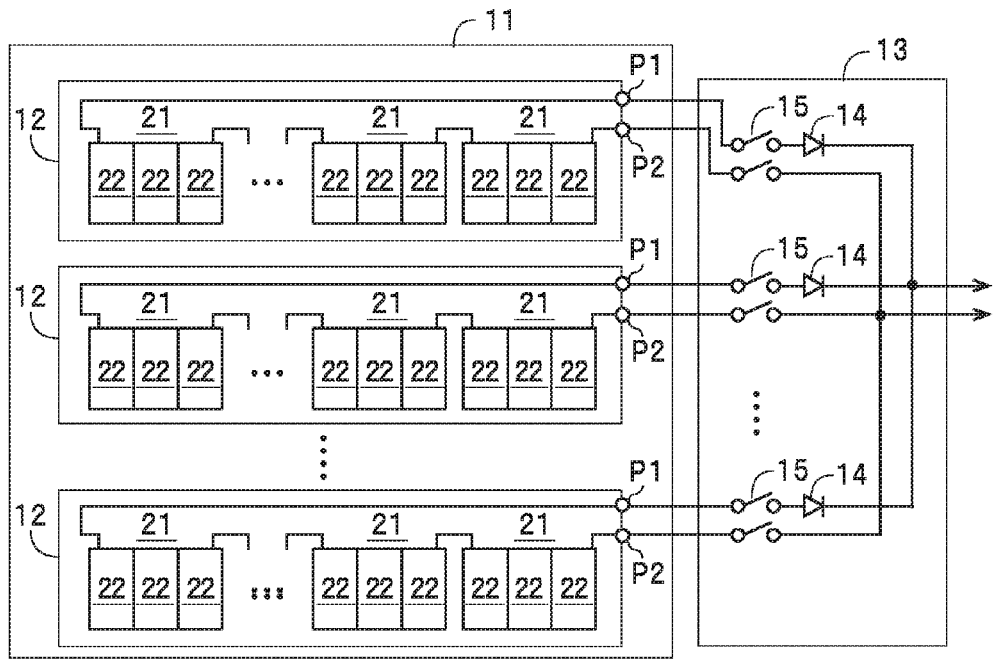
FIG. 2 depicts the configurations of a solar cell array and a junction box.

As shown in FIGS. 1 and 2, each solar cell string 12 is constructed by connecting a plurality of solar cell modules 21 in series, and each solar cell module 21 is constructed by connecting a plurality of clusters 22 in series. Each cluster 22 is constructed of a plurality of solar cells 23 that are connected in series and a bypass diode 24 that is connected between the output terminals of the plurality of solar cells 23 connected in series as a whole (i.e., between the output terminals of the cluster 22). The bypass diode 24 has a cathode terminal connected to the output terminal on the positive side of the plurality of solar cells 23 and an anode terminal connected to the output terminal on the negative side.

With this configuration, when the state of the plurality of solar cells 23 connected in series that construct a cluster 22 is such that it is difficult for a current (DC current) to flow from the output terminal on the negative side to the output terminal on the positive side (for example, a state where the cells become shaded by a tree), the bypass diode 24 allows a current inputted from another cluster 22 to pass by so that the outputting of a current (DC current) from the solar cell string 12 can continue.

Next, the respective component elements of the solar cell testing apparatus 1 will be described individually. As shown in FIG. 1, the diode 2 is connected between the positive electrode P1 and the negative electrode P2 of the solar cell string 12 with a polarity (polarity in the forward direction with respect to the output current Io) that permits passage of the output current Io outputted from the solar cell string 12 when the solar cells 23 are generating power. As one example in the present embodiment, the diode 2 is connected in series with the current detecting unit 4 and the switch 5, and a series circuit constructed by such component elements is connected between the positive electrode P1 and the negative electrode P2 of the solar cell string 12 via probes PL1, PL2, and the like. Since the current detecting unit 4 that detects the output current Io has the same fundamental configuration as a typical ammeter, the internal resistance will ideally be extremely close to zero ohms. Accordingly, when the switch 5 is switched to an ON state, the solar cell string 12 is shorted by the diode 2.

The voltage applying unit 3 is configured so as to be capable of applying a test voltage Vtst across the terminals of the diode 2 such that the cathode terminal of the diode 2 has a high potential relative to the potential of the anode terminal. With this configuration, when the solar cell testing apparatus 1 is connected to the solar cell string 12 and the solar cell string 12 is shorted by the diode 2 of the solar cell testing apparatus 1 (more specifically, by the series circuit composed of the diode 2, the current detecting unit 4, and the switch 5), the voltage applying unit 3 becomes able to apply the test voltage Vtst between the positive electrode P1 and the negative electrode P2 of the solar cell string 12 such that the negative electrode P2 has a high potential relative to the potential of the positive electrode P1.

Also, in the present embodiment, the voltage applying unit 3 is configured so as to be capable of outputting the test voltage Vtst with a voltage value in at least a range from an initial voltage value Vini to an upper limit voltage value Vmax. Here, when the forward direction voltage of the bypass diodes 24 disposed inside the various solar cell strings 12 to be subjected to testing is expressed as "Vf" and the number of bypass diodes 24 in the solar cell string 12 with the lowest number of bypass diodes 24 out of such various solar cell strings 12 is expressed as "n1", the initial voltage value Vini is a voltage value that slightly exceeds a voltage value produced by adding a voltage drop at a current limiting resistor 32, described later, to the sum (voltage: n1×Vf) of the forward direction voltages Vf of the n1 bypass diodes 24 that are connected in series. That is, the initial voltage value Vini is a voltage value likely to turn on the number n1 of bypass diodes 24 at the same time. When the number of bypass diodes 24 in the solar cell string 12 with the largest number of bypass diodes 24 is expressed as "n2", the upper limit voltage value Vmax is a voltage value calculated using the sum (voltage value: n2×Vf) of the forward direction voltages Vf of n2 bypass diodes 24.

More specifically, as depicted in FIG. 1, as one example the voltage applying unit 3 includes a series circuit SC composed of a capacitor 31 and the current limiting resistor 32 (a resistor that limits the current flowing during discharging of the capacitor 31 to an approximate current value), a power supply (DC power supply) 33, and a pair of switches 34 and 35 (single-pole, double-throw switches) as a switching unit. In this case, as one example, the series circuit SC is connected between the c contacts of the switches 34 and 35, the negative electrode of the power supply 33 is connected to the a contact of the switch 34, and the positive electrode of the power supply 33 is connected to the a contact of the switch 35. Also, the b contact (the position that functions as the output terminal of the voltage applying unit 3) of the switch 34 is connected to the anode terminal of the diode 2 and the b contact (the position that functions as the output terminal of the voltage applying unit 3) of the switch 35 is connected to the cathode terminal of the diode 2. Note that the switches 34 and 35 can be constructed of contact switches such as relays, or can be constructed of semiconductor switches (contactless switches) such as transistors or thyristors in order to avoid the occurrence of chattering when the switches are turned on and off.

The power supply 33 is constructed of a variable voltage power supply (unipolar power supply), for example, and is controlled by the processing unit 6 to output a DC voltage V1 with a voltage value set by the processing unit 6. The switches 34 and 35 are also controlled by the processing unit 6 and are selectively switched to one connection state out of a connection state (or "charging connection state") where the c contacts and the a contacts are connected and a connection state (or "discharging connection state") where the c contacts and the b contacts are connected.

With this configuration, in the voltage applying unit 3, when the switches 34 and 35 are controlled by the processing unit 6 and are switched to the charging connection state, the capacitor 31 that constructs the series circuit SC is charged by the DC voltage V1 outputted from the power supply 33 to the same voltage value V1 as the voltage value of the DC voltage V1 (such voltage value is also expressed by the symbol "V1" and referred to hereinafter as the "voltage value V1"). When the switches 34 and 35 in this state are controlled by the processing unit 6 and are switched to the discharging connection state, the voltage applying unit 3 applies the DC voltage V1 that stored in the capacitor 31 across the diode 2 (that is, across the solar cell string 12 that is shorted by the diode 2 when the switch 5 is in the on state) as the test voltage Vtst with the polarity described above. Note that since it is sufficient to supply enough power to charge the capacitor 31 as described above, the power supply 33 may be simply configured of a combination of a battery and the step-up circuit.

As described above, the current detecting unit 4 is connected, via the probes PL1 and PL2, between the positive electrode P1 and the negative electrode P2 of the solar cell string 12 in a state where the diode 2 and the switch 5 are connected in series. The current detecting unit 4 includes a current-to-voltage converting circuit, for example, detects a passing current and converts the current to the voltage and outputs the converted voltage to the processing unit 6 as a voltage signal Si (a signal whose voltage value changes in proportion to the current value of the passing current).

As one example, the switch 5 is constructed of a semiconductor switch (contactless switch), such as a transistor or a thyristor, to avoid arcing when the switch is turned on and off. According to control by the processing unit 6, the switch 5 is selectively switched to one state out of an on state and an of state. As described above, the switch 5 is connected, via the probes PL1 and PL2, between the positive electrode P1 and the negative electrode P2 of the solar cell string 12 in a state where the diode 2 and current detecting unit 4 are connected in series.

As one example, the processing unit 6 includes an A/D converter, a memory, a CPU, and the like, and is configured so as to be capable of executing control processes over the voltage applying unit 3 (more specifically, a process that sets the voltage value V1 of the DC voltage V1 of the power supply 33, a process that controls the starting and stopping of output of the DC voltage V1, and a process that switches the switches 34 and 33), a waveform measuring process that measures a current waveform of the current flowing in the current detecting unit 4 based on the voltage signal Si outputted from the current detecting unit 4, a control process for the switch 5 (a process that switches the switch 5), and a bypass diode testing process 50 (see FIG. 3) that tests the bypass diodes 24 of the solar cell string 12 connected as the tested object via the probes PL1 and PL2 to the solar cell testing apparatus 1 (a process that tests for the presence of bypass diodes 24 that have failed in the open position). Note that the initial voltage value Vini described above, the upper limit voltage value Vmax described above, and an increment (a unit voltage ΔV) used when gradually increasing the voltage value V1 of the DC voltage V1 (as one example in the present embodiment, the values is increased in steps) are stored in advance in the memory of the processing unit 6.

Also, the processing unit 6 is configured so as to be capable of executing an output process that outputs the result of the bypass diode testing process 50. For this output process, the solar cell testing apparatus 1 is provided with an output apparatus such as a display apparatus, and it is possible to output the result of the test to such output apparatus and/or to output the result of the test to another apparatus provided outside the solar cell testing apparatus 1.

Next, the operation of the solar cell testing apparatus 1 when testing the bypass diodes 24 of a solar cell string 12 using the solar cell testing apparatus 1, and a solar cell testing method will be described with reference to FIG. 3. Note that it is assumed that the respective solar cells 23 of the solar cell string 12 are normal.

When testing the bypass diodes 24 of a plurality of solar cell strings 12 that construct a solar cell array 11 installed on a building, an operation where a solar cell string 12 that is to be connected as a tested object to the solar cell testing apparatus 1 is cut off from the other solar cell strings 12 by switching a switch 15, out of the switches 15 in the junction box 13 connected to the solar cell array 11, corresponding to such solar cell string 12 from the on state to the off state, and the solar cell testing apparatus 1 is then connected via the probes PL1 and PL2 between the positive electrode P1 and the negative electrode P2 of such solar cell string 12 in the cut-off state is repeatedly carried out until the testing of the bypass diodes 24 of all of the solar cell strings 12 has been completed.

Figure 3:
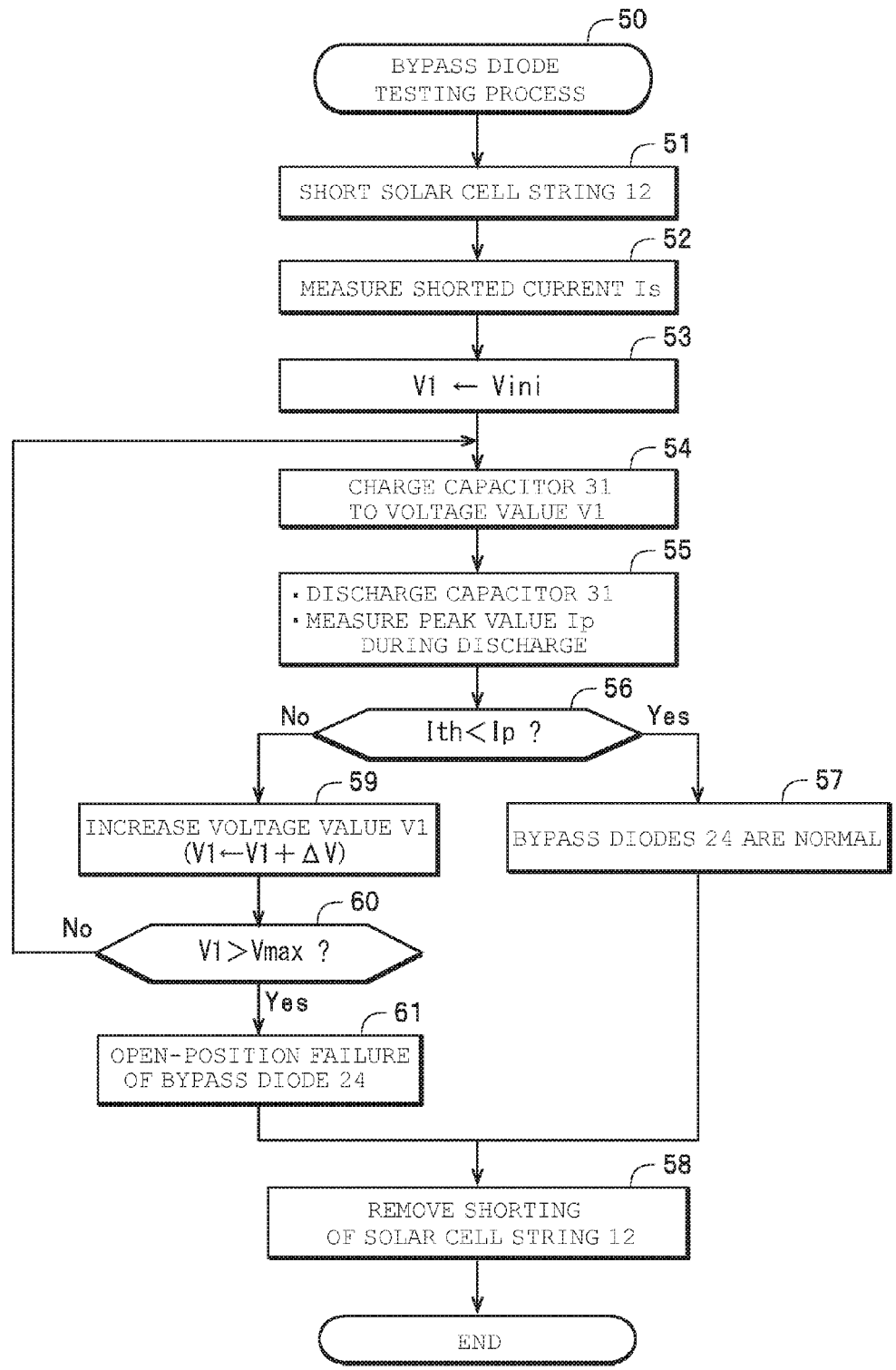
FIG. 3 is a flowchart useful in explaining the operation of the solar cell testing apparatus and a solar cell testing method.

With the solar cell testing apparatus 1, the bypass diode testing process 50 depicted in FIG. 3 is executed in a state where the solar cell string 12 (i.e., the solar cell string 12 including the bypass diodes 24 to be tested) to be tested is connected via the probes PL1 and PL2.

In the bypass diode testing process 50, the processing unit 6 first executes a process that shorts the solar cell string 12 (step 51). In this process, the processing unit 6 executes a control process over the switch 5 to switch the switch 5 that is off in an initial state to the on state. By doing so, the switch 5 in the on state and the current detecting unit 4 that is in a state where the internal resistance is extremely close to zero ohms, as well as the diode 2 with a polarity that permits passage of the output current Io from the solar cell string 12, become connected in series between the positive electrode P1 and the negative electrode P2 of the solar cell string 12 via the probes PL1 and PL2. This means that the solar cell string 12 is shorted by the series circuit composed of the diode 2, the current detecting unit 4, and the switch 5.

Next, the processing unit 6 executes a process that measures the output current Io outputted from the solar cell string 12 in the shorted state (since this is the output current Io in the shorted state, this current is also referred to as the "shorted current Is") (step 52). More specifically, in this process, the processing unit 6 first executes a waveform measuring process that measures and stores the current waveform (see FIG. 4) of the shorted current Is flowing in the current detecting unit 4 based on the voltage signal Si outputted from the current detecting unit 4. Next, the processing unit 6 measures the current value of the shorted current Is based on the stored current waveform and stores a current value that is slightly higher than the measured current value (for example, a current value that is several percent higher) as a current threshold Ith (see FIG. 4) used when testing the bypass diodes 24. Here, in a period that is sufficiently shorter than the time required for the insolation on the solar cell string 12 to change, such as the time required by one iteration of the bypass diode testing process 50 (since it is effectively enough to observe the discharge waveform of the capacitor 31, several milliseconds to several tens of milliseconds including the time required to measure the shorted current Is), it is possible to regard the insolation on the solar cell array 11 as substantially constant. This means that the shorted current Is has a current waveform of a DC current with a substantially constant current value, as shown by the solid line in FIG. 4.

Note that whenever the bypass diode testing process 50 is executed, by using a configuration that measures and stores the current threshold Ith, it is possible to adjust (i.e., increase or decrease) the current threshold Ith in keeping with changes in insolation on the solar cell array 11 (that is, the amount of sunshine on the solar cell string 12), which means that it is possible to improve the precision of the testing of the bypass diodes 24 that uses this current threshold Ith as described later.

Next, the processing unit 6 executes a control process over the voltage applying unit 3 and sets the voltage value V1 of the DC voltage V1 outputted from the power supply 33 at the initial voltage value Vini (step 53).

Next, the processing unit 6 executes a control process over the voltage applying unit 3 to charge the capacitor 31 to the DC voltage V1 (step 54). More specifically, in step 54, the processing unit 6 first executes a process that switches the switches 34 and 35 to connect the series circuit SC composed of the capacitor 31 and the current limiting resistor 32 to the power supply 33 and then has the power supply 33 start outputting the DC voltage V1. By doing so, the capacitor 31 is charged to the DC voltage V1 (i.e., to a state where the switch 35 side terminal reaches a potential that is the voltage value V1 higher than the potential of the switch 34 side terminal).

Next, the processing unit 6 executes a control process over the voltage applying unit 3, connects the capacitor 31 to the diode 2, has the capacitor 31 discharged, and measures the maximum current value (peak value) Ip of the current flowing in the current detecting unit 4 during discharging of the capacitor 31 (step 55). More specifically, in step 55, the processing unit 6 executes a process that switches the switches 34 and 35 and connects the series circuit SC composed of the capacitor 31 and the current limiting resistor 32 to the diode 2. By doing so, the DC voltage V1 stored in the capacitor 31 is applied to the diode 2 in a state where the potential of the cathode terminal is at a high potential compared to the potential of the anode terminal and in turn is applied as the test voltage Vtst to the solar cell string 12 that is shorted by the diode 2. After applying the test voltage Vtst, the processing unit 6 executes a control process over the voltage applying unit 3 to stop the power supply 33 outputting the DC voltage V1.

The processing unit 6 executes the waveform measuring process for a time set in advance from the start of application of the test voltage Vtst, measures the current waveform of the current flowing in the current detecting unit 4 based on the voltage signal Si outputted from the current detecting unit 4, and measures and stores the maximum current value (peak value) Ip of the current flowing in the current detecting unit 4 based on such current waveform.

After this, the processing unit 6 compares the measured peak value Ip with the current threshold Ith stored in step 52 (step 56).

Here, as depicted in FIG. 1, the test voltage Vtst is applied to every bypass diode 24 in the plurality of bypass diodes 24 in the solar cell string 12 with polarity such that the anode terminal becomes a nigh potential relative to the cathode terminal (i.e., the voltage is applied in the forward direction). This means that when the test voltage Vtst has a voltage value that exceeds the sum of the forward direction voltage values Vf of the plurality of the bypass diodes 24 in the solar cell string 12 being tested (first condition) and when all of the bypass diodes 24 are normal (second condition), all of the bypass diodes 24 are turned on by the application of the test voltage Vtst.

Figure 4:
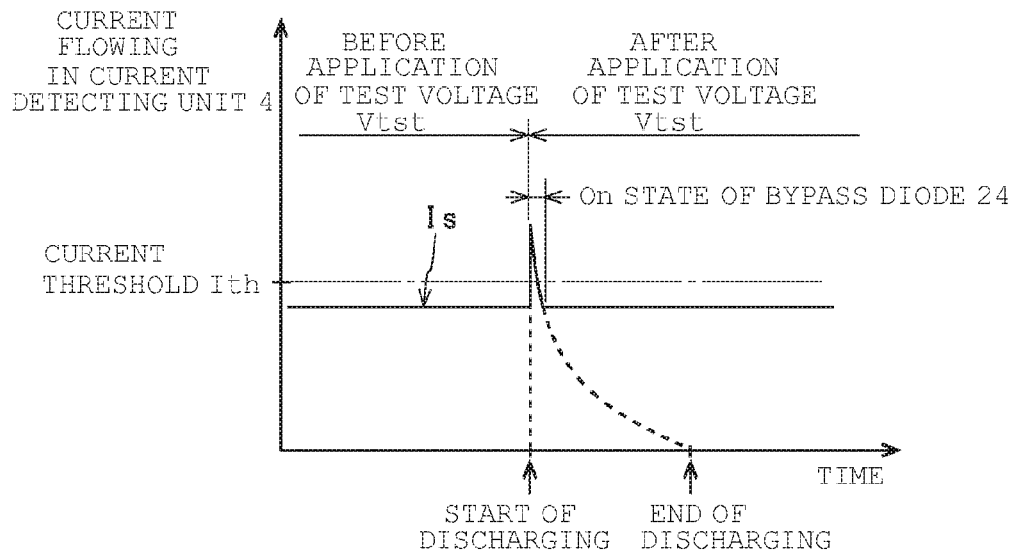
FIG. 4 is a waveform chart (a waveform chart for when the bypass diodes are normal) useful in explaining the operation of the solar cell testing apparatus and the solar cell testing method.

Accordingly, when doing so, the charge applied to the capacitor 31 flows on a current path from the voltage applying unit 3 that reaches the voltage applying unit 3 via the negative electrode P2 of the solar cell string 12, the bypass diodes 24 in the on state that are connected in series in the solar cell string 12, the positive electrode P1 of the solar cell string 12, the switch 5 in the on state, and a current detecting unit 42, so that for a period immediately after application of the test voltage Vtst, as depicted in FIG. 4, a peak that exceeds the current waveform of the shorted current Is appears in the current waveform of the current flowing in the current detecting unit 4. Also, as described above, by setting the current threshold Ith at a current value that is slightly higher than the current value of the shorted current Is, in most cases the peak value Ip of the peak will exceed the current threshold Ith.

On detecting, as a result of the comparison in step 56, a state where the peak value Ip that exceeds the current threshold Ith, the processing unit 6 determines that all of the bypass diodes 24 in the solar cell string 12 being tested are normal, executes the output process, and outputs a test result showing that the bypass diodes 24 are normal (step 57). Note that when, as a result of the stored charge being discharged, the voltage of the capacitor 31 falls to the sum of the forward direction voltage values Vf of the bypass diodes 24 or below, all of the bypass diodes 24 return from the on state to the off state, which means that as shown in FIG. 4, the current flowing in the current detecting unit 4 returns to the shorted current Is from the solar cell string 12. In such case, the charge remaining in the capacitor 31 flows as part of the shorted current Is (i.e., the discharging of the capacitor 31 continues) and the voltage of the capacitor 31 gradually decreases and reaches substantially zero volts (more specifically, the forward direction voltage of the diode 2).

After executing step 57, the processing unit 6 executes a control process over the switch 5 to switch the switch 5 to the off state (i.e., the initial state). By doing so, the shorting of the solar cell string 12 by the series circuit composed of the diode 2, the current detecting unit 4, and the switch 5 is removed (step 58) and the bypass diode testing process 50 is completed.

Figure 5:
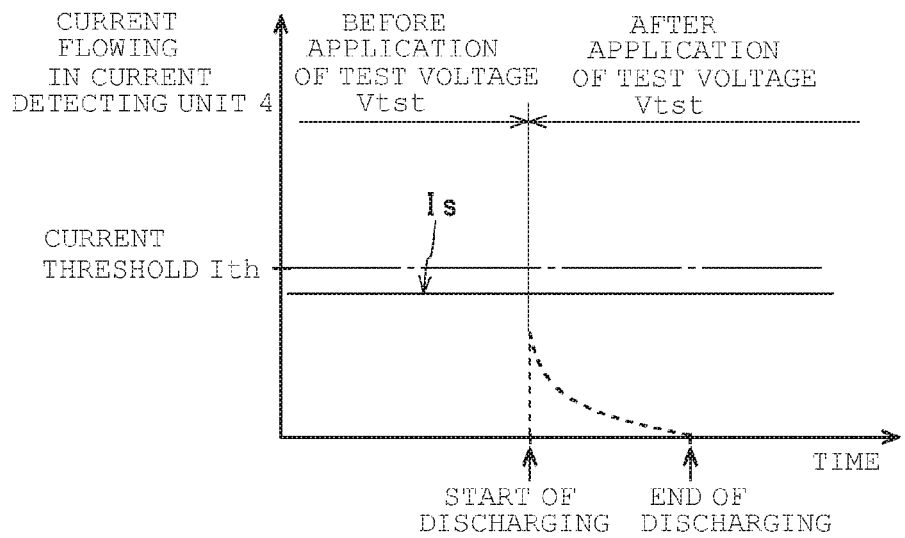
FIG. 5 is a waveform chart (a waveform chart for when one of the bypass diodes has failed in the open position) useful in explaining the operation of the solar cell testing apparatus and the solar cell testing method.

On the other hand, when, as the result of the comparison in step 56, it is detected that the peak value Ip is equal to or below the current threshold Ith (in reality, since it is not possible to observe peaks that are smaller than the shorted current Is, when a shorted current Is in which no peak appear has been observed), the processing unit 6 determines that the first condition described above is not satisfied, that is, the test voltage Vtst has not reached the sum of the forward direction voltage values Vf of the plurality of bypass diodes 24 in the solar cell string 12, and calculates, as a new candidate voltage value V1 for the DC voltage V1, a voltage value obtained by adding the unit voltage ΔV stored in the memory to the present voltage value V1 (step 59). Not that in this case, as depicted in FIG. 5, since the current produced due to the discharging of the capacitor 31 depicted by the broken line flows as part of the shorted current Is, during the discharging state of the capacitor 31 also, the current detected by the current detecting unit 4 is the shorted current Is from the solar cell string 12 only. The capacitor 31 also continues to discharge, and the voltage gradually decreases and reaches substantially zero volts (more specifically, the forward direction voltage of the diode 2).

In this way, when a new higher voltage value V1 has been calculated, the processing unit 6 compares the new voltage value V1 and the upper limit voltage value Vmax stored in the memory and determines whether the voltage value V1 exceeds the upper limit voltage value Vmax (step 60). When, as a result, the voltage value V1 does not exceed the upper limit voltage value Vmax (when V1>Vmax is not satisfied), the processing unit 6 proceeds to step 54 described above and by executing the control process over the voltage applying unit 3, the capacitor 31 is charged by the DC voltage V1 with the new voltage value V1.

After this, while repeatedly executing step 54, step 55, step 56, step 59, and step 60, if the result of the comparison in step 56 is that "the peak value Ip exceeds the current threshold Ith" before the new voltage value V1 calculated in step 59 exceeds the upper limit voltage value Vmax in the comparison in step 60, the processing unit 6 determines that all of the bypass diodes 24 in the solar cell string 12 being tested are normal and outputs such test result (step 57), removes the shorting of the solar cell string 12 (step 58), and completes the bypass diode testing process 50.

On the other hand, if, during the repeated execution of step 54, step 55, step 56, step 59, and step 60, the processing unit 6 detects that the new voltage value V1 calculated in step 59 has exceeded the upper limit voltage value Vmax in the comparison in step 60 before the result of the comparison in step 56 is that "the peak value Ip exceeds the current threshold Ith", the processing unit 6 determines that at least one bypass diode 24 in the solar cell string 12 being tested has failed in the open position and executes the output process to output a test result indicating such result (step 61).

The reason for determining that there is a failure in the open position is as follows. Irrespective of the first condition described above being satisfied (that is, when, even for the solar cell string 12 with the largest (n2) number of bypass diodes 24 out of the solar cell strings 12 to be tested, the upper limit voltage value Vmax exceeds the sum (n2×Vf) of the forward direction voltage Vf of such bypass diodes 24), the bypass diodes 24 do not enter the on state because the second condition described above (that is, the condition that all the bypass diodes 24 are normal) is not satisfied, that is, at least one of the bypass diodes 24 in the solar cell string 12 being tested has failed in the open position. In this case, the charge of the capacitor 31 flows as part of the shorted current Is and the voltage of the capacitor 31 gradually falls and reaches substantially zero volts (more specifically, the forward direction voltage of the diode 2).

After executing step 61, the processing unit 6 executes control over the switch 5 and switches the switch 5 to the off state (i.e., the initial state). By doing so, the shorting of the solar cell string 12 by the series circuit composed of the diode 2, the current detecting unit 4, and the switch 5 is removed (step 58) and the bypass diode testing process 50 is completed.

In this way, with the solar cell testing apparatus 1 and the solar cell testing method described above, when testing the bypass diodes 24 in a solar cell string 12 for failures in the open position, in a state where the diode 2 is connected between the positive electrode P1 and the negative electrode P2 of the solar cell string 12 with polarity that permits the passage of the output current Io outputted from the solar cell string 12 when the solar cells 23 are generating power, a test voltage Vtst with the voltage value V1 that exceeds the sum of the forward direction voltages Vf of the plurality of bypass diodes 24 and is such that the potential of the negative electrode P2 is higher than the potential of the positive electrode P1 is applied between the positive electrode P1 and the negative electrode P2 of the solar cell string 12 to which the diode 2 is connected (i.e., the solar cell string 12 that is shorted by the connected diode 2), and a test for failures in the open position is performed for the bypass diodes 24 by comparing the currents detected by the current detecting unit 4 before and after application of the test voltage Vtst (in the example described above, by comparing the current threshold Ith decided based on the shorted current Is before application of the test voltage Vtst and the peak value Ip of the current after application of the test voltage Vtst).

Accordingly, according to the solar cell testing apparatus 1 and the solar cell testing method described above, even when the solar cell string 12 (that is, the solar cells 23) are generating power and the open-circuit voltage is extremely high (as one example, around 1000V for the largest solar cell strings 12, where the number of solar cell modules 21 connected in series is 30 and three clusters 22 are connected in series in each solar cell module 21), by shorting the diode 2, it is sufficient for the test voltage Vtst for turning on the plurality of bypass diodes 24 in a solar cell string 12 to be a low voltage that is only slightly higher than the sum of the forward direction voltages Vf of the bypass diodes 24 (in the example described above, the number of bypass diodes 24 in one solar cell string 12 is 90 (=30×3), and if the forward direction voltage Vf is 0.6V, for example, the sum will be 54V, which is an extremely low voltage compared to 1000V). This means that it is possible to easily and reliably test bypass diodes for failures in the open position, even when a solar cell string is generating power.

Also, according to the solar cell testing apparatus 1 and the solar cell testing method described above, it is possible, as in the example described above, to produce the voltage applying unit 3 of the series circuit SC with a simple configuration composed of the capacitor 31 and the current limiting resistor 32, the power supply 33, and the pair of switches 34 and 35 (single-pole, double-throw switches) as a switching unit, without using an expensive power supply such as a bipolar power supply. This means that the solar cell testing apparatus 1 can be manufactured at low cost.

Also, with the solar cell testing apparatus 1 and the solar cell testing method described above, the processing unit 6 executes control over the voltage applying unit 3 to gradually increase the charging voltage (voltage value V1) of the capacitor 31 while applying such voltage as the test voltage Vtst until the charging voltage reaches the upper limit voltage value Vmax set in advance. As described above, the number of bypass diodes 24 provided in a solar cell string 12 being tested may differ depending on the solar cell array 11 installed on a building. Here, although it would be conceivable to use a configuration where the upper limit voltage value Vmax, which is capable of turning on the bypass diodes 24 in a solar cell string 12 with the highest number of bypass diodes 24 out of the solar cell strings 12 to be tested, is applied from the start as the test voltage Vtst, with such a configuration, an excessive test voltage Vtst would be applied to a solar cell string 12 with a low number of bypass diodes 24, for example, and due to this an overcurrent would flow to the bypass diodes 24, which could cause one or more bypass diodes 24 to fail.

On the other hand, according to the solar cell testing apparatus 1 and the solar cell testing method described above, since it is possible to gradually increase the test voltage Vtst applied from the voltage applying unit 3 to the solar cell string 12, by stopping the application of the test voltage Vtst as soon as it has been detected that the bypass diodes 24 are normal by comparing the currents before and after application of the test voltage Vtst detected by the current detecting unit 4, it is possible to prevent failure of the bypass diodes 24 due to the application of an excessive test voltage Vtst.

Note that it should be obvious that when testing a solar cell string 12 for which the number of internally-provided bypass diodes 24 is known, in place of a configuration that gradually increases the test voltage Vtst applied to the solar cell string 12, it is possible to use a configuration that applies a test voltage Vtst calculated from the sum of the forward direction voltages Vf of such bypass diodes 24 from the start.

Figure 6:
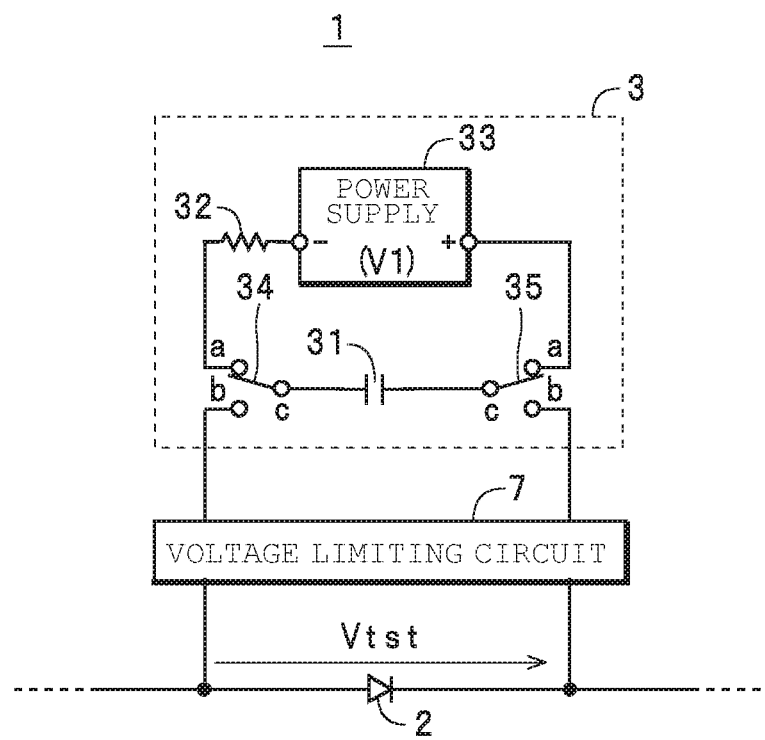
FIG. 6 depicts part of the configuration of a solar cell testing apparatus in which a voltage limiting circuit is disposed.

Also, as depicted in FIG. 6, it is also possible to use a configuration where a voltage limiting circuit 7, which limits the upper limit of the current flowing in the bypass diodes 24 due to the application of the test voltage Vtst to a limit value, is disposed in the current circuit. Note although FIG. 6 depicts a configuration where the voltage limiting circuit 7 is disposed outside the voltage applying unit 3, it is also possible to use a configuration where the voltage limiting circuit 7 is disposed inside the voltage applying unit 3. When the voltage limiting circuit 7 is provided, by setting the limit value of the voltage limiting circuit 7 below the peak forward current of the bypass diodes 24, it is possible, even when a variety of solar cell strings 12 with different numbers of bypass diodes 24 are tested, to use a configuration where the upper limit voltage Vmax that is capable of turning on the bypass diodes 24 in the solar cell string 12 with the highest number of bypass diodes 24 out of the solar cell strings 12 to be tested is applied from the start as the test voltage Vtst while still avoiding failure of the bypass diodes 24 due to an overcurrent. Although detailed information on the bypass diodes used in solar cell modules is typically not released by module makers and it is difficult to know the peak forward current, by considering the purpose of bypass diodes which is to enable a generated current to bypass failed clusters and continue flowing, the shorted current indicated in the specification of a solar cell module will definitely be able to flow in such module. For this reason, it is desirable to limit the limit value of the voltage limiting circuit 7 to double the shorted current Is observed in step 52 (i.e., the shorted current Is plus the current flowing in the bypass diodes) (this refers to the voltage limiting circuit 7 being controlled by the processing unit 6). In this case, the current limiting resistor 32 that constructs the series circuit SC of the voltage applying unit 3 depicted in FIG. 1 is not needed during discharging. On the other hand, when the capacitor 31 is being charged by the power supply 33, it is necessary to limit the charging current. Accordingly, a configuration is used where in place of the location depicted in FIG. 1, the current limiting resistor 32 is disposed at at least one of a location between the power supply 33 and the switch 34 as depicted in FIG. 6 and a location between the power supply 33 and the switch 35 (not illustrated). With this configuration, it is possible to test for bypass diodes 24 that have called in the open position by a single application of the test voltage Vtst, which makes it possible to reduce the time required for testing.

Also, as described above, when testing the bypass diodes 24 of a plurality of solar cell strings 12 that construct a single solar cell array 11 installed on a building, an operation where one solar cell string 12 to be tested is cut off from the other solar cell strings 12 and connected to the solar cell testing apparatus 1 is executed for every solar cell string 12. This means that with the solar cell testing apparatus 1 and the solar cell testing method described above, it is possible to acquire current waveforms when the test voltage Vtst is applied to each solar cell string 12. Accordingly, it is also possible to detect a change in impedance (or extent of deterioration) of the bypass diodes 24 by comparing the peak value Ip of the current flowing in the bypass diodes 24 of a solar cell string 12 that is normal with other solar cell strings 12.

Also, in the example described above, although a configuration where the current threshold Ith decided based on the shorted current Is before application of the test voltage Vtst is compared with the peak value Ip of the current after application of the test voltage Vtst is used as one example of a configuration that compares the currents detected by the current detecting unit 4 before and after application of the test voltage Vtst, it is also possible to use a configuration that compares the waveforms of the currents detected by the current detecting unit 4 before and after application of the test voltage Vtst while focusing on the appearance of a spiked (peaked) waveform in the waveform of the current detected by the current detecting unit 4 as depicted in FIG. 4 when all of the bypass diodes 24 are normal and the absence of such spiked (peaked) waveform when one of the bypass diodes 24 has failed in the open position as depicted in FIG. 5.

The location of the current detecting unit 4 is not limited to the location depicted in FIG. 1. The current detecting unit 4 may be disposed at an arbitrary position on a current path (a current path that reaches the negative electrode P2 of the solar cell string 12 from the positive electrode P1 via the switch 5 and the voltage applying unit 3) of the spiked current that flows when the bypass diodes 24 are turned on due to the application of the test voltage Vtst. Accordingly, it is possible to dispose the current detecting unit 4 on the side of the voltage applying unit 3 connected to both ends of the diode 2. More specifically, it is possible to dispose the current detecting unit 4 at one location out of a location between the b contact of the switch 34 and the anode terminal of the diode 2 and a location between the b contact of the switch 35 of the cathode terminal of the diode 2. In addition, it is possible to dispose the current detecting unit 4 in series with the series circuit SC inside the voltage applying unit 3 (i.e., it is possible to integrate the current detecting unit 4 in the voltage applying unit 3).

Also, as described above, although the solar cell string 12 is typically constructed by connecting a plurality of solar cell modules 21 in series, for a solar cell array 11 constructed of a solar cell module 21 with a single solar cell string 12, the solar cell string 12 to be tested will be the solar cell module 21 itself.

What is claimed is:

1. A solar cell testing apparatus that tests bypass diodes in a solar cell string constructed by connecting a plurality of solar cell modules, which include solar cells and the bypass diodes, in series for failures in the open position, the solar cell testing apparatus comprising:
   a unidirectional element that is connected between a positive electrode and a negative electrode of the solar cell string with a polarity that permits passage of an output current outputted from the solar cell string when the solar cells generate power;
   a voltage applier capable of applying a test voltage, which has a voltage value that exceeds a sum of forward direction voltages of a plurality of bypass diodes and is a voltage such that a potential of the negative electrode is high relative to a potential of the positive electrode, across the positive electrode and the negative electrode of the solar cell string to which the unidirectional element is connected;
   a current detector that detects a current flowing in the solar cell string; and
   a processor that tests for failures in the open position by comparing the currents detected by the current detector before and after application of the test voltage in a state where the unidirectional element is connected between the positive electrode and the negative electrode of the solar cell string.

2. The solar cell testing apparatus according to claim 1, wherein the voltage applier includes: a series circuit composed of a capacitor and a current limiting resistor; a power supply; and a switch that switches between a charging connection state where the series circuit is connected to the power supply and a discharging connection state where the series circuit is connected between the positive electrode and the negative electrode of the solar cell string, and
   when switching to the charging connection state, the switch is controlled to connect the power supply to the series circuit and the capacitor is charged using a DC voltage outputted from the power supply, and when switching to the discharging connection state, the switch is controlled to connect the series circuit between the positive electrode and the negative electrode of the solar cell string and a charging voltage of the capacitor that was charged in the charging connection state is applied between the positive electrode and the negative electrode as the test voltage.

3. The solar cell testing apparatus according to claim 2, wherein the processor executes control over the voltage applier to apply the charging voltage as the test voltage while gradually increasing the charging voltage until a upper limit voltage value set in advance is reached.

4. A solar cell testing method that tests bypass diodes in a solar cell string constructed by connecting a plurality of solar cell modules, which include solar cells and the bypass diodes, in series for failures in the open position, the solar cell testing method comprising:

applying, in a state where a unidirectional element is connected between a positive electrode and a negative electrode of the solar cell string with a polarity that permits passage of an output current outputted from the solar cell string when the solar cells generate power, a test voltage, that has a voltage value that exceeds a sum of forward direction voltages of a plurality of the bypass diodes and is a voltage such that a potential of the negative electrode is high relative to a potential of the positive electrode, across the positive electrode and the negative electrode of the solar cell string to which the unidirectional element is connected while detecting a current flowing in the solar cell string; and testing for failures in the open position by comparing the current before and after application of the test voltage in the state where the unidirectional element is connected between the positive electrode and the negative electrode.

* * * * *